United States Patent [19]

Barbour, Jr.

[11] 4,284,209
[45] Aug. 18, 1981

[54] DEVICE AND METHOD FOR COLLECTING BLOOD PLASMA

[76] Inventor: Robert E. Barbour, Jr., 1904 Bunch Dr., Fort Worth, Tex. 76112

[21] Appl. No.: 50,668

[22] Filed: Jun. 21, 1979

[51] Int. Cl.³ .............................................. B65D 35/28
[52] U.S. Cl. ........................................ 222/1; 222/43; 222/48; 222/103; 128/214F
[58] Field of Search ................... 222/41, 43, 48, 103, 222/1; 128/214 R, 214 F, 226, DIG. 12

[56] References Cited

U.S. PATENT DOCUMENTS

| | | | |
|---|---|---|---|
| 1,965,596 | 7/1934 | Kline | 222/103 X |
| 2,903,161 | 9/1959 | Stahmer | 222/103 X |
| 3,565,292 | 2/1971 | Jinotti | 222/103 |
| 3,595,232 | 7/1971 | Leibinsohn | 128/214 F |
| 3,734,351 | 5/1973 | Gaudin | 222/103 |
| 3,960,294 | 6/1976 | Bernard | 222/103 |

*Primary Examiner*—David A. Scherbel
*Attorney, Agent, or Firm*—James E. Bradley

[57] ABSTRACT

A method and device for forcing segregated plasma from a flexible collecting bag containing a layer of plasma over a layer of red blood cells has a member to reduce the chance for a portion of the red blood cells to also flow from the collecting bag. The device has a fixed member mounted normal to a base, and a movable member connected to the base by a hinge and urged toward the fixed member by a spring. The spring squeezes the collecting bag, which is supported between the fixed and movable members, forcing the plasma from the top of the bag. A stop member automatically stops the movement of the movable member when a large portion of the plasma has been forced from the bag. The stop member is releasable, allowing further movement of the movable member to remove the remaining portion of the plasma while being closely monitored by an operator.

8 Claims, 3 Drawing Figures

DEVICE AND METHOD FOR COLLECTING BLOOD PLASMA

BACKGROUND OF THE INVENTION

1. Field of the Invention

This invention relates in general to a device and method for removing plasma from a flexible bag containing a layer of plasma over a layer of red bood cells.

2. Description of the Prior Art

Blood plasma is used to manufacture a number of medical products. In donation centers, the whole blood is collected conventionally in a flexible clear bag. Then while the donor waits, the bag of whole blood is placed in a centrifuge. The blood will separate into two layers, with a plasma layer above the red blood cell layer. The plasma is fairly clear and makes up about sixty percent of the whole blood.

The operator then places the segregated bag into an extractor device. The extractor device has a fixed plate and a spring loaded movable plate, with the bag being supported vertically between them. The bag is squeezed between the plates by spring force, with the plasma being forced out the top through a tube and into a collection bag. Once substantially all of the plasma is forced out, the spring pressure is released. The red blood cells are then fed back into the donor. Returning the red blood cells to the donor allows the donor to donate twice per week. If the red blood cell portion cannot be returned, the donor must wait eight weeks before donating again.

During the extraction process, the operator observes the bag and releases the pressure when he sees that the plasma has nearly all flowed from the bag. The process of forcing the fluid from the bag takes about three to seven minutes, and one operator may have several bags being extracted at the same time, as well as controlling the centrifuge. Consequently, the operator may inadvertently allow some of the red blood cells to escape into the bag collecting the plasma by failing to release the spring pressure at the proper time. If contamination occurs, the contaminated plasma must be centrifuged again to separate the red blood cells. The recentrifuged plasma is again placed in an extractor device and forced out of the bag. During this second operation, some of the plasma cannot be squeezed from the bag, and will be lost.

Also, a contamination error is a hazard to the donor. Red cells are oxygen carriers and have a short life at room temperatures. The red blood cells that inadvertently were allowed to flow into the plasma collecting bag will be lost. They cannot be returned to the donor after recentrifuging because due to the time loss they will probably be dead. If a large amount of red blood cells are lost, the donor will be unable to return for eight weeks. Consequently, not only does a contamination error result in additional time being spent by the operator in recentrifuging the collected plasma, but it also results in a loss of expensive plasma and may cause donor disqualification.

SUMMARY OF THE INVENTION

It is accordingly a general object of this invention to provide an improved method and device for removing plasma from a bag containing a layer of plasma and a layer of red blood cells.

It is a further object of this invention to provide an improved method and device for removing plasma from a bag containing a layer of plasma and a layer of red blood cells, in a manner that reduces the chance for contamination of the plasma with red blood cells.

In accordance with these objects, a device is provided of the type having a base, an upright fixed member, and a movable member that closes against the fixed member. The bag is supported by the upright fixed member. A stop means is secured to one of the members for stopping further closing movement of the movable member at a point selected to occur when a large portion of the plasma has been forced from the bag. The stop means is releasable to allow further flow of plasma while the bag is being monitored by the operator. Consequently, when commencing the extraction, the operator places the stop means in an interfering position so that it will automatically stop when most, but not all, of the plasma has been forced from the bag. The operator then will release the stop means, and closely observe the bag while the remaining portion of the plasma is forced from the bag.

DESCRIPTION OF THE PREFERRED EMBODIMENT

Figure 1:
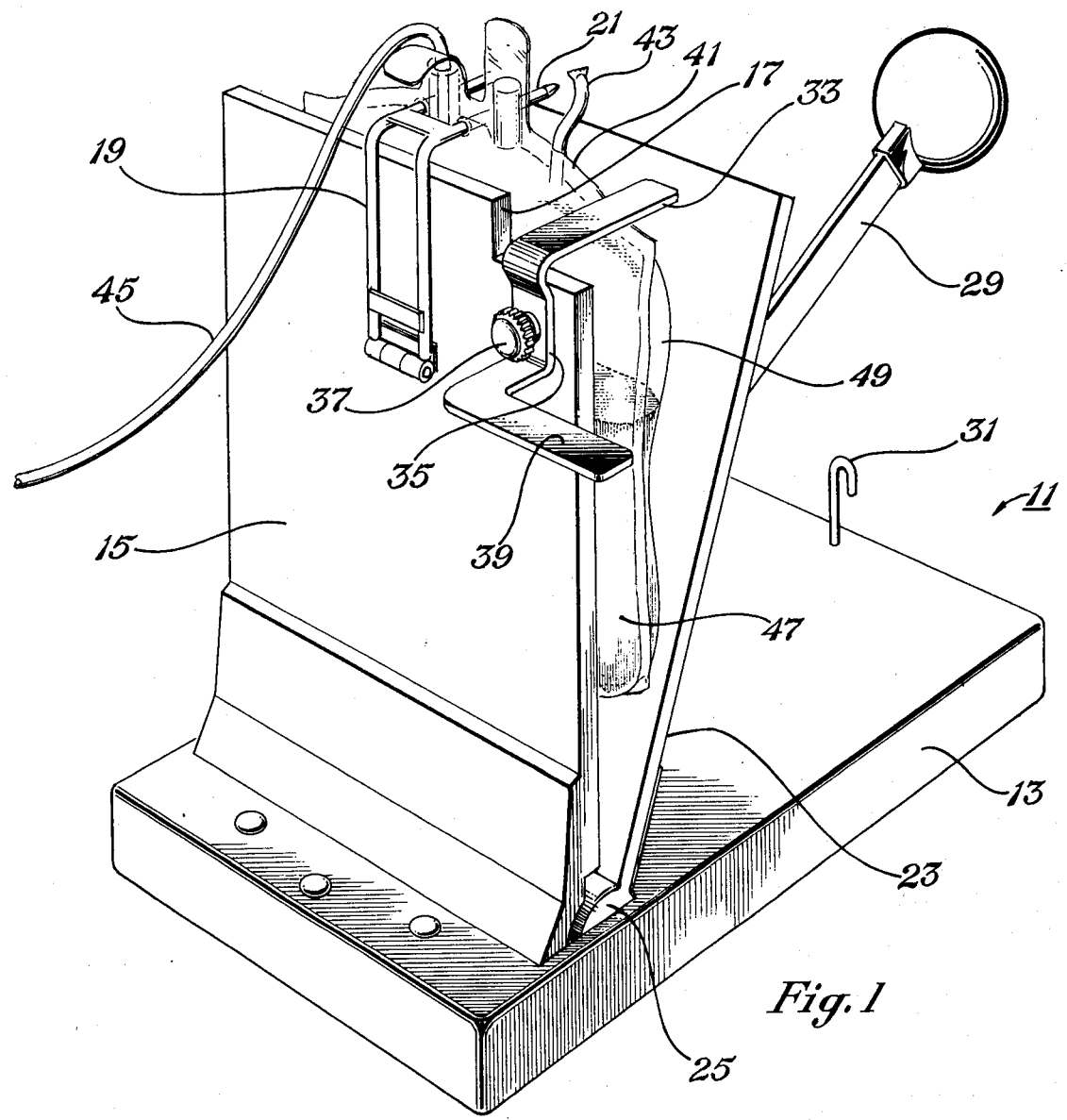
FIG. 1 is a perspective view of a device for extracting plasma from a bag, constructed in accordance with this invention.
Figures 2, 3:
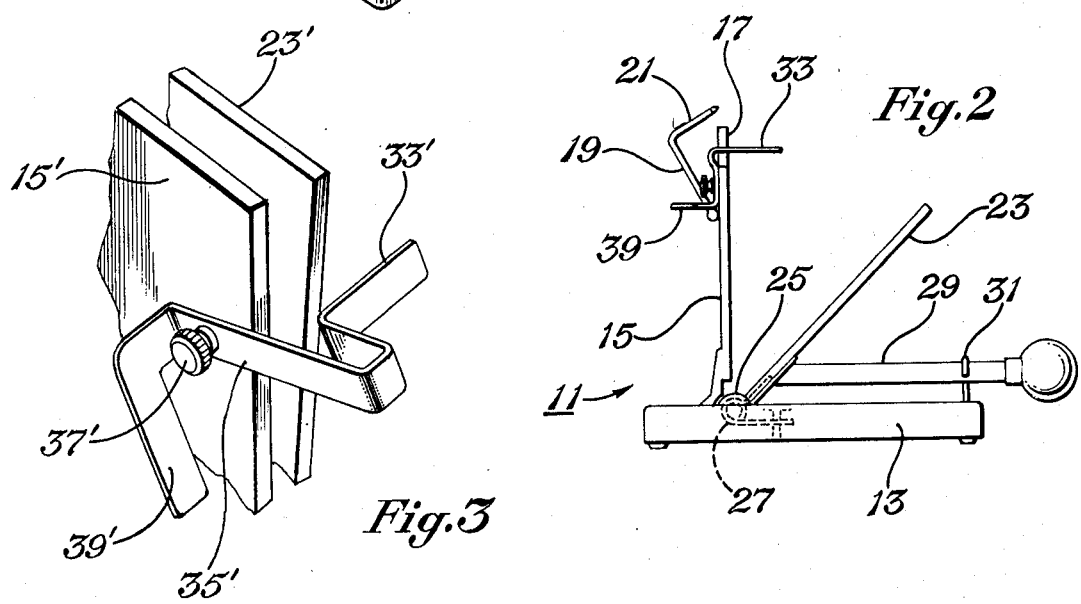
FIG. 2 is a side elevational view of the device of FIG. 1, shown in the open position.
FIG. 3 is an alternate embodiment of the device of FIG. 1.

Referring to FIG. 1, device 11 includes a flat, horizontal supporting base 13. A fixed member or plate 15 is rigidly secured to base 13 normal to it. Fixed plate 15 is rectangular, and flat. In the embodiment of FIG. 1, the upper right hand corner has a small rectangular shoulder or notched portion, indicated by numeral 17. A hanger 19 is pivotally secured to the back of fixed plate 15. Hanger 19 comprises two rods extending up over the upper edge of fixed plate 15, with free ends 21 extending horizontally past the fixed plate 15. As shown in FIG. 2, hanger 19 can be pivoted back for attaching and detaching a collection bag.

A movable plate 23 is connected to base 13 by a hinge 25, located at the bottom of fixed plate 15. As shown in FIG. 2, hinge 25 has a spring 27 secured to it to serve as spring means for urging the movable plate 23 towards the fixed plate 15. Movable plate 23 is a thin flat plate of substantially the same dimensions as fixed plate 15, however it does not have a notched portion 17. Movable plate 23 is rotatable about hinge 25 in a vertical plane, from the open position shown in FIG. 2, to a position in which it closes against and is in substantial contact with fixed plate 15. A handle 29 is secured to the back of movable plate 23 for allowing the operator to stop movement of movable plate 23 and pull it back to the open position. A hook 31 is secured in base 13 for engaging handle 29 in the open position, to retain it in the open position.

Stop means for preventing further closing movement of movable plate 23 includes a finger 33 extending generally toward movable plate 23 and perpendicular to an integral intermediate portion 35. Intermediate portion 35 is pivotally secured to fixed plate 15 on the outer side of and immediately below notched area 17 by a screw and nut 37. Intermediate portion 35 is parallel with fixed plate 15. An arm 39 is formed integrally with the intermediate portion 35. Arm 39 is generally "L" shaped, with a first portion extending away from fixed plate 15 perpendicular to intermediate portion 35. A second portion extends laterally in a direction 90° degrees from the direction in which the free end of finger 33 points. Finger 33 is positioned so that its free end extends into the path of movable plate 23 when the finger is in the interfering position, as shown in FIG. 1. Once movable plate 23 contacts the free end of finger 33, it will be prevented from further closing movement. Moving arm 39 downwardly pivots finger 33 out of the path of the movable plate 23, allowing further closing movement. Finger 33 along with its vertical portion 35 and arm 39 are flat strips of metal. Screw and nut 37 allow pivoting without having to loosen them.

Device 11 is adapted to receive a conventional bag 41 for collecting blood. Bag 41 is a clear, flexible, plastic type container having a tube 43 for receiving incoming fluid. A tube 45, is adapted to be secured to an outlet in the top of bag 41. Bag 41 is adapted to fit on the free ends 21 of hanger 19, which serves as support means for retaining the bag in a vertical orientation. As is shown in the lightly shaded areas in FIG. 1, bag 41 after centrifuging contains a portion, indicated as 47, that represents the red blood cell portion of whole blood, and another portion, indicated as 49, that represents the plasma portion of whole blood. The portions 47 and 49 will separate by centrifuging into distinct layers with very little mixing at the intersection of the layers.

In operation, the whole blood is collected from the donor through tube 43. Tube 43 is then sealed and the bag is placed in a centrifuge. The centrifuge spins the bag at a high rate of speed, causing the whole blood to segregate into a lighter weight plasma portion 49 over a layer of heavier red blood cells 47. The operator then places the bag on the free ends 21 of hanger 19 and connects it to a collecting bottle for plasma (not shown) by tube 45. During this time, handle 29 will be secured in hook 31. Once the bag 41 is in position, handle 29 is moved out of hook 31, allowing spring 27 to urge the movable plate 23 toward the fixed plate 15. The pressure will squeeze bag 41, forcing the plasma 49 to flow out tube 45. At the same time that the closing movement is initiated, arm 39 is rotated into a horizontal position, placing finger 33 into the path of movable plate 23, as shown in FIG. 1. The plasma 49 uniformly makes up about sixty percent of the whole blood. The length and position of finger 33 has been empirically selected, considering this, to cause movable plate 23 to contact finger 33 when approximately ninety percent of the plasma 49 has been forced from bag 41. Contact of finger 33 will cease further closing movement of the movable plate 23. Once stopped, the operator will rotate arm 39 downwardly to shift finger 33 out of the interfering position, releasing movable plate 23 to further compress bag 41. Since already ninety percent of the plasma 49 has been extracted from bag 41, the operator must closely monitor the flow of plasma during this last stage. Once the operator determines that no more plasma can be forced from the bag 41 without causing also some red blood cell portion 47 to flow from bag 41, he will stop further movement. The operator will grasp handle 29 and rotate movable plate 23 downwardly, fixing it into the open position and securing handle 29 by means of hook 31. The bag 41 is then removed from the device 11, and the red blood cell portion 47 is fed back into the donor.

FIG. 3 represents an alternate embodiment of the stop means. Fixed plate 15' does not have a notched portion 17. Rather finger 33' has a portion that extends over the upper edge of the fixed plate 15', then bends forwardly for contacting movable plate 23', when in the interfering position. The finger intermediate portion 35' and arm 39' are of the same configuration. Nut and screw 37' are positioned close to the vertical side of fixed plate 15, so that when arm 39' is rotated downwardly, as shown in FIG. 3, finger 33' will be in a noninterfering position.

It should be apparent than an invention having significant improvements has been provided. The stop means prevents further movement of the movable plate once a large portion of the plasma has been removed. Consequently, this allows the operator to occupy himself with other tasks during the extraction of the plasma, without the fear that contamination will occur in his absense. Once the stop means has stopped the movable plate from further closing movement, the operator can, at his convenience, extract the remaining small portion of plasma while closely monitoring it to avoid contamination. This allows the operator to handle many more extractors than previously. It also reduces the chances for contamination, which causes plasma loss, and if severe enough, donor disqualification due to red blood cell loss.

While the invention has been shown in only two of its forms, it should be apparent to those skilled in the art that it is not so limited but is susceptible to various changes and modifications without departing from the spirit thereof.

I claim:

1. In a device for forcing segregated plasma from a flexible collecting bag containing a layer of plasma over a layer of red blood cells, the device being of the type having a base, a fixed member secured normal to the base, a movable member connected to the base by a hinge and rotatable about the hinge to substantially close against the fixed member, spring means for urging the movable member toward the fixed member, and support means for retaining the bag between the fixed and movable members, the improvement comprising:
   stop means secured to one of the members for stopping further closing movement of the movable member at a point selected to occur when a large portion of plasma has been forced from the bag;
   the stop means being releasable to allow further closing movement of the movable member and further flow of plasma from the bag while being monitored by an operator to assure that the further closing movement is stopped prior to the flow of red blood cells from the bag.

2. The device according to claim 1 wherein the stop means comprises:
   a finger pivotally secured to one of the members, having an interfering position wherein it will contact the other member, and a noninterfering position wherein it will not interfere with the movement of the movable member.

3. The device according to claim 2 wherein the finger is secured to the fixed member adjacent one corner.

4. The device according to claim 1 wherein the stop means comprises:
   a finger having a portion pivotally secured to the outer side of the fixed member, and a free end protruding past the fixed member into the path of the movable member for contacting it; and an arm extending from the finger laterally outward past the fixed member, the finger being secured to the fixed member in a position that causes the finger to move out of the path of the movable member when the arm is rotated downward.

5. An improved device for forcing segregated plasma from a flexible bag containing a layer of plasma over a layer of red blood cells, comprising:
   a base;
   a fixed member secured normal to the base;
   a movable member connected to the base by a hinge and rotatable about the hinge to substantially close against the fixed member;
   spring means for urging the movable member toward the fixed member;
   support means attached to the fixed member for supporting the bag in a vertical orientation on the fixed member between the fixed member and the movable member;
   a finger pivotaly secured to one of the members and pointing generally toward the other member so that it will contact the other member to prevent further movement of the movable member;
   the length and positioning of the finger being selected to cause cessation of movement of the movable member when a large portion of the plasma has been forced from the bag, the finger being pivotal into a noninterfering position to allow further closing movement of the movable member while being monitored by an operator.

6. The device according to claim 5 wherein the finger is secured to the fixed member, and further comprising an arm extending laterally from the finger at its connection with the fixed member, for pivoting the finger.

7. The device according to claim 6 wherein the fixed member and the movable member each comprise flat plates.

8. In a method of removing plasma from a flexible bag containing a layer of plasma over a layer of red blood cells, the method including the steps of placing the bag between a fixed member and a movable member, and urging the movable member toward the fixed member to squeeze the bag and force fluid from the top, the improvement comprising:
   positioning a stop member between the fixed and movable members to automatically stop closing movement at a point selected to occur when a large portion of the plasma has been forced from the bag; then
   releasing the stop member to allow further closing movement of the movable member; and
   monitoring the movement after the stop member has been released to manually stop movement of the movable member when substantially all of the plasma has flowed from the bag and prior to any red cells flowing from the bag.

* * * * *